United States Patent
Rogalsky

(10) Patent No.: US 6,987,019 B1
(45) Date of Patent: Jan. 17, 2006

(54) DEVICE FOR GROWING CELLS

(75) Inventor: Vitaly Rogalsky, 186 Pinehurst Ave. #3D, New York, NY (US) 10033

(73) Assignee: Vitaly Rogalsky, New York, NY (US)

( * ) Notice: Subject to any disclaimer, the term of this patent is extended or adjusted under 35 U.S.C. 154(b) by 0 days.

(21) Appl. No.: 10/934,178

(22) Filed: Sep. 3, 2004

(51) Int. Cl.
*C12M 3/04* (2006.01)

(52) U.S. Cl. ............... 435/299.2; 435/304.2; 206/456; 211/41.14

(58) Field of Classification Search ............. 435/288.1, 435/288.2, 299.1, 299.2, 304.1–304.3; 422/102, 422/104; 206/456; 211/41.14
See application file for complete search history.

(56) References Cited

U.S. PATENT DOCUMENTS

| | | | |
|---|---|---|---|
| 3,532,605 A | 10/1970 | Riera | 195/139 |
| 3,853,712 A | 12/1974 | House et al. | 195/127 |
| 3,941,661 A | 3/1976 | Noteboom | 195/127 |
| 4,024,975 A | 5/1977 | Uhlig | 215/1 C |
| 4,121,976 A | 10/1978 | Gleeson | 195/104 |
| 4,228,243 A * | 10/1980 | Iizuka | 435/294.1 |
| 4,234,089 A * | 11/1980 | Morris | 206/456 |
| 4,665,035 A | 5/1987 | Tunac | 435/296 |
| 4,734,373 A | 3/1988 | Bartal | 435/296 |
| 4,790,361 A | 12/1988 | Jones et al. | 150/55 |
| 4,824,757 A | 4/1989 | Aono et al. | 430/169 |
| 5,084,390 A | 1/1992 | Hallewell et al. | 435/188 |
| 5,167,366 A | 12/1992 | Desmarais et al. | 236/49.3 |
| 5,190,878 A * | 3/1993 | Wilhelm | 435/297.2 |
| 5,270,205 A * | 12/1993 | Rogalsky | 435/298.1 |
| 5,310,676 A | 5/1994 | Johansson et al. | 435/285 |
| 6,305,543 B1 * | 10/2001 | Lafond et al. | 206/456 |
| 6,569,675 B2 | 5/2003 | Wall et al. | 435/304.2 |
| 2004/0029267 A1 * | 2/2004 | Martin et al. | 435/299.1 |

FOREIGN PATENT DOCUMENTS

DE     3413707 A1 * 10/1985
JP     62264636 A * 11/1987

* cited by examiner

*Primary Examiner*—William H. Beisner
(74) *Attorney, Agent, or Firm*—I. Zborovsky

(57) ABSTRACT

A device for growing cells has a container with a bottom; and a plurality of elements extending into an area for growing cells and formed as thin, elongated plates extending along the bottom one after the other at predetermined distances from one another.

7 Claims, 7 Drawing Sheets

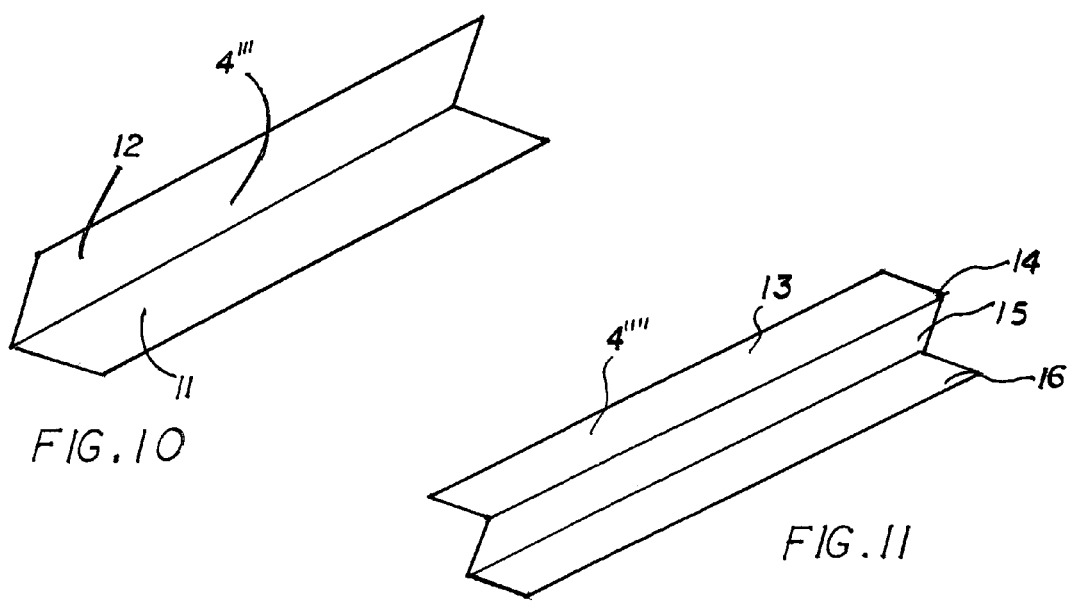
FIG. 10
FIG. 11
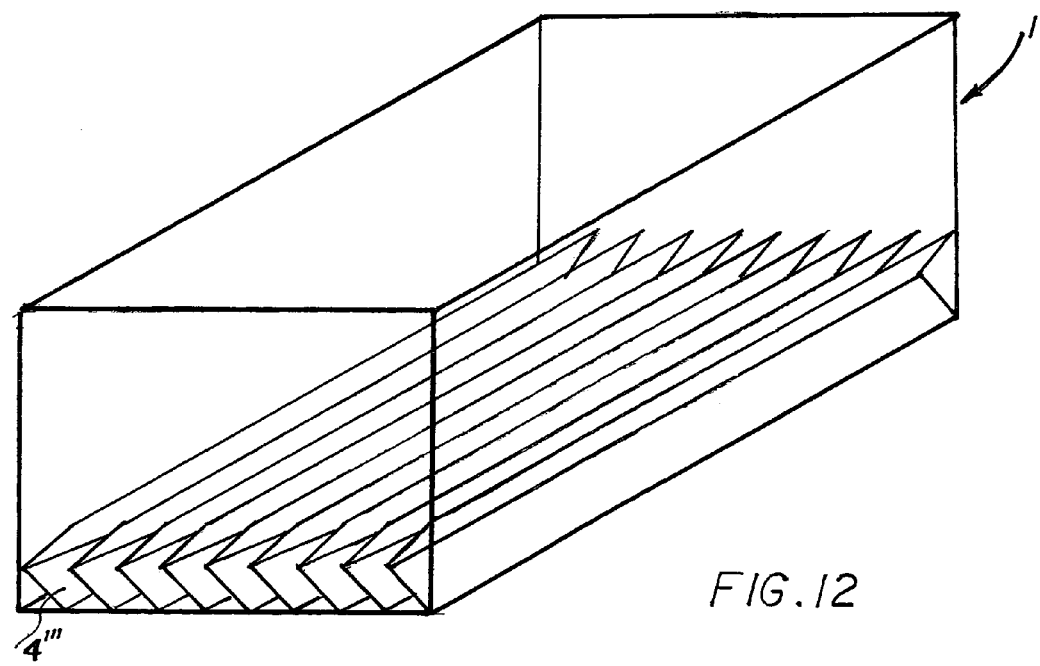
FIG. 12

DEVICE FOR GROWING CELLS

BACKGROUND OF THE INVENTION

The present invention relates to a device for growing cells.

Devices of the above-mentioned general type are known in the art. Some of such devices are disclosed in U.S. Pat. Nos. 3,532,605; 3,853,712; 3,941,661; 4,024,975; 4,121,976; 4,665,035; 4,734,373; 4,790,361; 4,824,757; 5,084,390; 5,167,366; 5,310,676 and 6,569,675. It is believed that the existing devices can be further improved, in particular by increasing the area for growing of cells.

SUMMARY OF THE INVENTION

Accordingly, it is an object of the present invention to provide a device for growing cells, which is a further improvement in the existing devices.

In keeping with these objects and with others which will become apparent hereinafter, one feature of the present invention resides, briefly stated, in a device for growing cells, comprising a container having a bottom; and a plurality of elements extending into an area for growing cells and formed as thin, elongated plates extending along said bottom one after the other at predetermined distances from one another.

When the device is designed in accordance with the present invention, it provides an extended, large surface for attaching cells to the plates and for growing cells in a corresponding biological medium.

The novel features which are considered as characteristic for the present invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWINGS

FIGS. 5–14 are views showing further embodiments of the inventive device for growing cells position;

DESCRIPTION OF THE PREFERRED EMBODIMENTS

Figure 1:
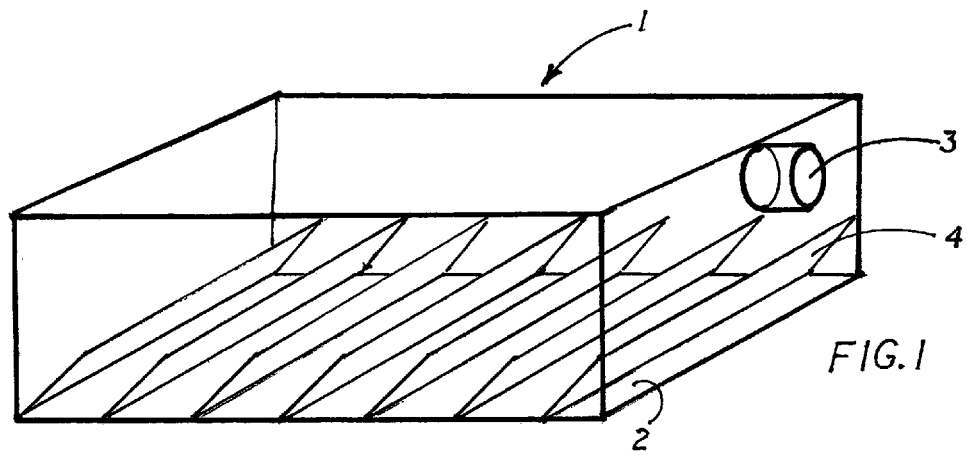
FIG. 1 is a view showing a device for growing cells in accordance with one embodiment of the present invention.

A device for growing cells in accordance with the present invention shown in FIG. 1 has a container, which is identified as a whole with reference numeral 1. The container has a bottom 2 and a plurality of walls, and also a conduit or part 3 for introduction of a biological media with cells into the container 1 and withdrawal of the same from the container 1. The device shown in FIG. 2 is provided with an openable lid 5 for the same purpose.

In accordance with one embodiment of the present invention, the device further has a plurality of elements on which cells are attached and can grow, and which are formed as thin plates extending into an area for growing cells of the container. The plates 4 can be connected or not connected with the container. For example, they can be produced together with the bottom of the container, or can be attached to the bottom of the container by any known means.

Figure 2:
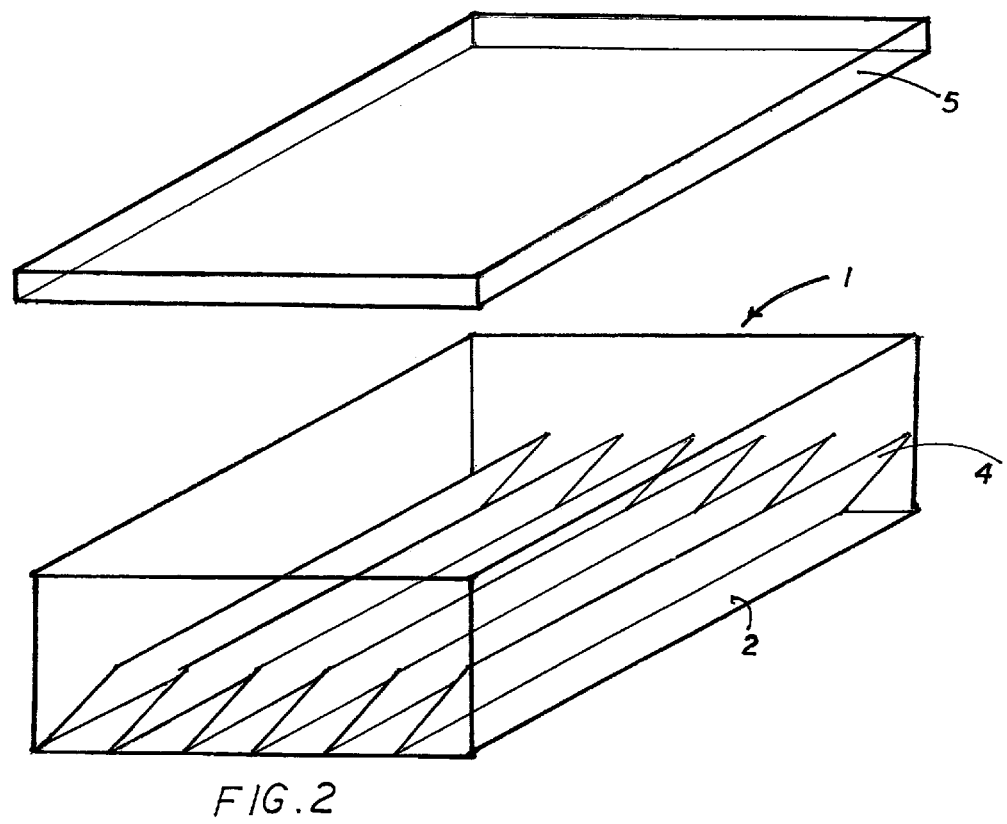
FIG. 2 is a view showing a device for growing cells in accordance with another embodiment of the present invention.

In the embodiment shown in FIG. 1, the plates are formed so that they extend transversely over the container 1 which has a substantially parallelepiped-like shape, white in FIG. 2 the elements 4 are formed so that they extend in a longitudinal direction of the container 1. It is also possible that they extend diagonally, or along any direction.

Figure 3:
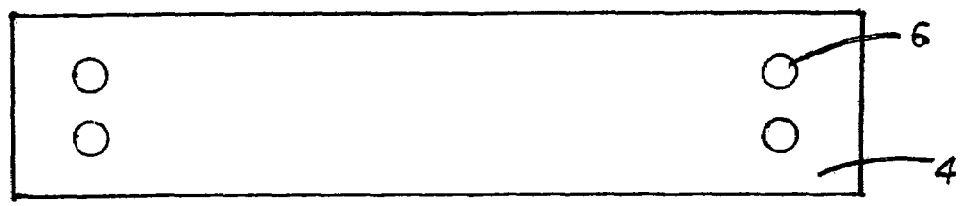
FIG. 3 is a view showing an element of the inventive device for growing cells in accordance with a further embodiment of the present invention.
Figure 4:
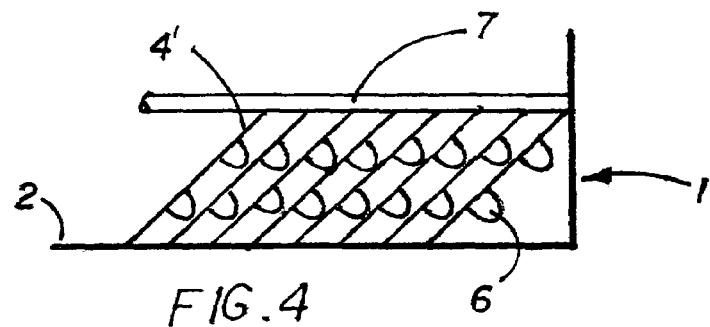
FIG. 4 shows the device provided with the elements shown in FIG. 3.
Figure 5:
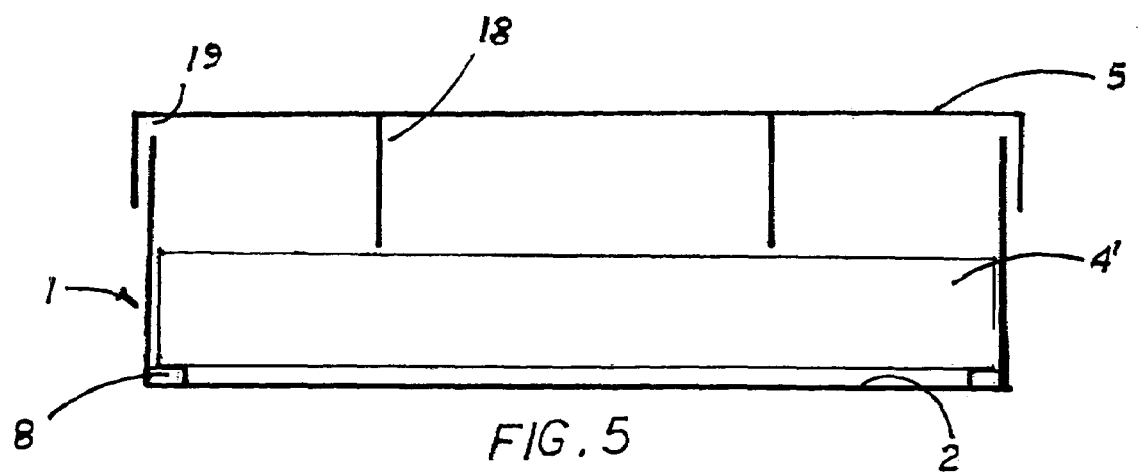

As shown in FIGS. 3 and 4, the plates 4' can have protrusions 6 which form spacers between them. An upward movement can be limited by a partition 7 which can be braced between the device walls or could be part of lid, as shown on FIG. 5 the element 18.

Figure 14:
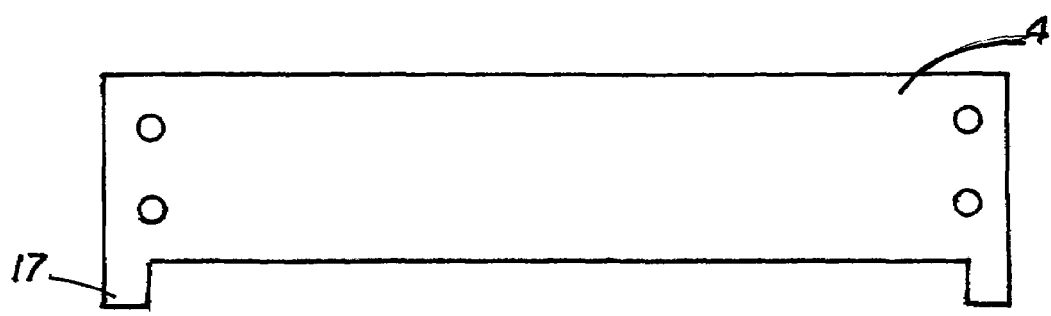

A space can be provided between the strips and the bottom 2, for example by use of bottom spacers 8 (FIG. 5) or legs 17 on the plates (FIG. 14).

As shown in FIGS. 1 and 2, the plates 4 and 4' are inclined relative to the bottom 2 so that the cells can attach to the plates and grow on them. In accordance with a preferable embodiment of the present invention, the plates 4 and 4 are inclined relative to one another at such an angle that one of the plates overlaps a neighboring one of the plates so that the one plate hangs over the other plates. The plates thus form a structure, which resembles scales.

Figure 6:
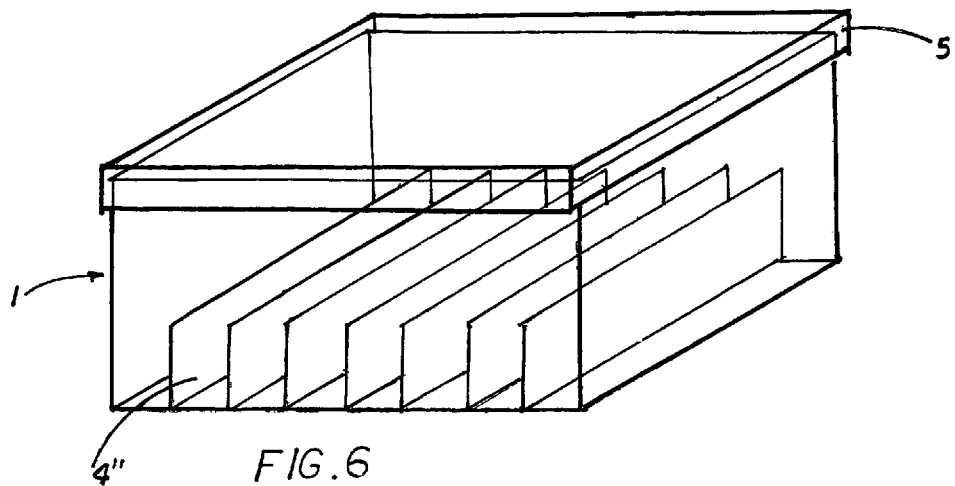
Figure 7:
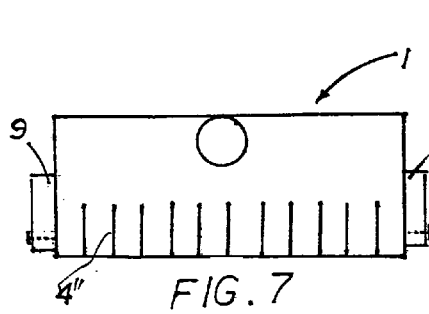
Figure 8:
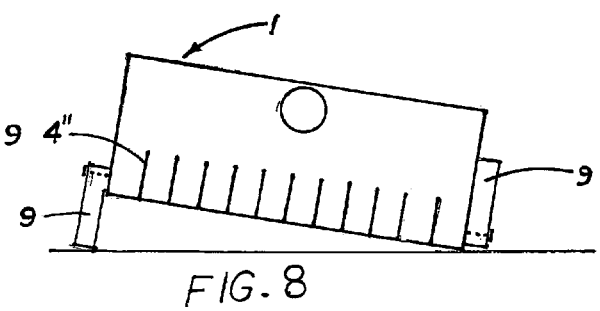

In the embodiment shown in FIG. 6 the elements for growing cells are also formed as elongated thin plates 4", which however are, arranged perpendicular to the bottom 2 of the container 1. In order to provide an inclined arrangement of the plates 4", the container as a whole is inclined. For this purpose, the container can be provided with inclination means formed for example, as legs identified with reference numeral 9. In FIG. 7 the container is originally arranged substantially horizontally. Then, as shown in FIG. 8, the left leg is turned around a pivot point and extended downwardly, so that the left side of the container is located higher than the right side of the container, and the bottom of the container is inclined to provide the inclination of the plates 4".

Figure 9:
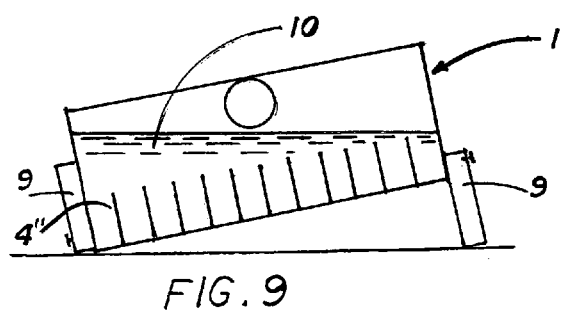

As shown in FIG. 9, the right leg of the container is pivoted about its axis so that the right side of the container is lifted, while the left side of the container remains the same to provide the inclination of the bottom of the container and therefore an inclined orientation of the plates. As shown in FIG. 9, with the inclined orientation of the container the plates 4"-assume an inclined orientation as well, and a biological medium 10 covers the inclined plates 4" to provide growing of the cells. The inclination of the device can be also provided by placement of the device on an inclined shelf.

As shown in FIG. 10, each plate 4''' can be composed of two portions 11 and 12 which are connected with one another along the longer sides so as to form a pleat-shaped plate. In the embodiment shown in FIG. 11, each plate 4''' is composed of several such portions 13, 14, 15 so as to form more than one pleat. FIG. 12 shows the pleat-shaped plates 4''' extending from the bottom of the container 1. This further increases a useful area for attachment and growing of the cells in the container 1.

Figure 13A:
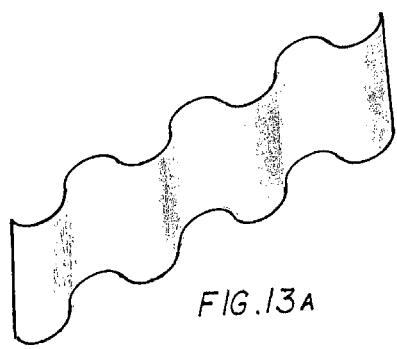
Figure 13B:
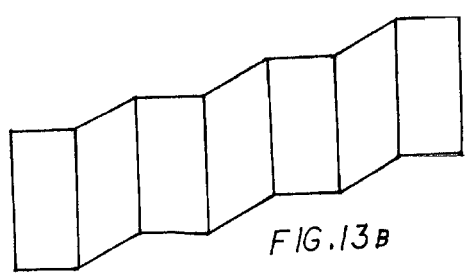
Figure 13C:
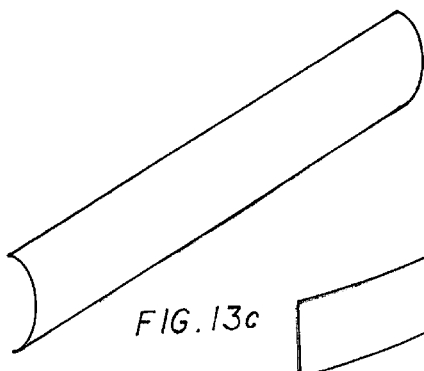
Figure 13D:
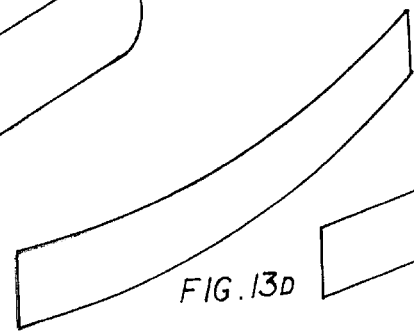
Figure 13E:
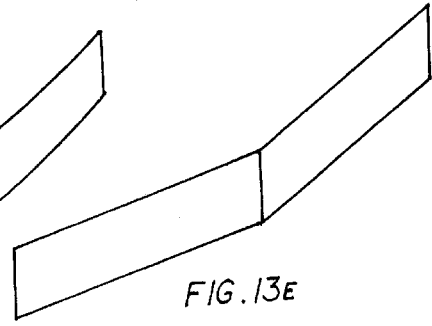

In accordance with further embodiments of the present invention shown in FIGS. 13A–13E, the plates can be non-straight in a direction of their elongation for example waved (FIG. 13*a*), pleated (FIG. 13B), curved transversely to the plates (FIG. 13C), curved along the plates (FIG. 13D), bent along the plates (FIG. 13E).

The strips of the device can have protrusions and corrugations of different types.

Figure 15:
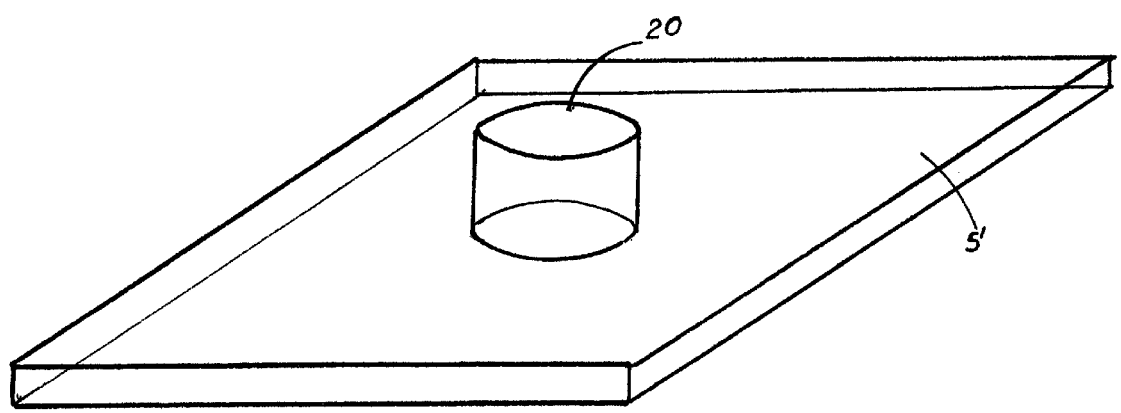
FIG. 15 shows a special lid for the device for growing cells.

FIG. 15 shows a special lid 5' for the container. There is space 19 (FIG. 5) between container and the lid. The space provides effective gas exchange in the device. The lid can be fixed to a container or can be attached loosely. The lid has a conduit part 20 (FIG. 15) for introduction of biological media with cells.

It will be understood that each of the elements described above, or two or more together, may also find a useful application in other types of constructions differing from the types described above.

While the invention has been illustrated and described as embodied in a device for growing cells, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

What is claimed is:

1. A device for growing cells, comprising a container having a flat horizontal bottom; and a plurality of elements for growing cells, located in an area for growing cells and being formed as thin, elongated plates which are spaced at predetermined distances from one another in a horizontal direction and inclined relative to said horizontal bottom, said plates having two opposite sides and being provided on one of said sides with lateral protrusions configured to provide said predetermined distances between said plates in said horizontal direction.

2. A device as defined in claim 1, wherein said plates are arranged so that a space remains between said flat bottom and said plates; and further comprising means for maintaining said space and including bottom spacers provided on said flat bottom in an area between said flat bottom and side walls of said container.

3. A device as defined in claim 1, wherein said plates are arranged so that they are spaced from said flat bottom; and further comprising means for maintaining a space between said plates and said bottom and including legs provided on lower part of said plates.

4. A device as defined in claim 1, wherein said container also has side walls and a top wall, said top wall being formed as a removable, substantially flat lid which extends over a whole horizontal dimension of said container and which can be removed for withdrawal of said plates from said container to collect cells.

5. A device as defined in claim 4, wherein said lid has a conduit part for introduction of a biological media with cells.

6. A device as defined in claim 5, and further comprising a horizontal partition provided between said lid and said bottom and formed as a part of said lid so as to hold said plates from above.

7. A device as defined in claim 1, wherein said container has side walls which extend vertically over a height which is greater than a height of said plates so that said plates are located below an upper edge of said side walls of said container to be completely immersed in a medium for growing cells.

* * * * *